United States Patent [19]
Maloney et al.

[11] Patent Number: 6,162,632
[45] Date of Patent: Dec. 19, 2000

[54] OXLT SEQUENCE AND ITS USE

[75] Inventors: Peter C. Maloney, Baltimore, Md.; Keietsu Abe, Noda, Japan; Zhong-Shi Ruan, Cranbury, N.J.

[73] Assignee: Johns Hopkins School of Medicine

[21] Appl. No.: 09/030,267

[22] Filed: Feb. 25, 1998

Related U.S. Application Data

[60] Provisional application No. 60/038,345, Feb. 27, 1997.

[51] Int. Cl.$^7$ ....................................................... C12N 1/20
[52] U.S. Cl. ..................................... 435/252.3; 435/320.1; 435/325; 435/193; 435/232; 536/23.1; 536/23.2; 536/23.7
[58] Field of Search ................................. 536/23.1, 23.7, 536/23.2; 435/320.1, 252.3, 325, 193, 232

[56] References Cited

PUBLICATIONS

H.L. Lung et al., "Cloning and Expression of the Oxalyl--CoA Decarboxylase Gene From the Bacterium, Oxalobacter formigenes: Prospects for Gene Therapy to Control Ca–Oxalate Kidney Stone Formation", Amer. J. Kidney Diseases XVII(4): 381–385, Apr. 1991.

K. Abe et al. "Exchange of Aspartate and Alanine", J.Biol. Chem. 271(6): 3079–3084, Feb. 1996.

Laine et al., "Stable Transformation of the Gram–Positive Phytopathogenic Bacterium *Clavibacter michiganensis* subsp. *sepedonicus* with Several Cloning Vectors," *Applied and Environmental Microbiology*, vol. 62, No. 5 (May 1996), pp. 1500–1506.

Fu et al. "Evaluation of Secondary Structure of OxlT, the Oxalate Transporter of *Oxalobacter formigenes*, by Circular Dichroism Spectroscopy," *The Journal of Biological Chemistry*, vol. 272, No. 4 (Jan. 24, 1997), pp. 2129–2135.

Ruan et al. "Identification, Purification, and Reconstitution of OxlT, the Oxalate:Formate Antiport Protein of *Oxalobacter formigenes*," *The Journal of Biological Chemistry*, vol. 267, No. 15 (May 25, 1992), pp. 10537–10543.

*Primary Examiner*—Rebecca E. Prouty
*Attorney, Agent, or Firm*—Alston & Bird LLP

[57] ABSTRACT

A DNA sequence encoding a transport protein responsible for the physical movement of oxalate and formate across the plasma membrane is provided. The protein, OxlT, can be isolated from the gram negative anaerobe, *Oxalobacter formigenes*. The protein is part of the three protein oxalate/formate antiport exchange system that allows for conversion of extracellular oxalate to formate+$CO_2$.

The OxlT coding sequence can be used to provide a metabolic energy system to the cell. The system comprises the OxlT transport protein in combination with oxalylCoA decarboxylase and formyl-CoA transferase. Expression cassettes can be designed to express all or part of the system in a target host. Such energy generating systems can be used in industrial settings that utilize fermentation. The energy generating systems of the invention extend culture longevity and increase product yield.

In another aspect of the invention, the OxlT coding sequence can be used in pharmaceutical compositions for manipulating serum oxalic acid levels in patients in need thereof. In this manner, liposomes comprising the energy generating system can be developed and administered to humans and other animals.

12 Claims, 4 Drawing Sheets

FIG. 1.

```
   1 ATG AAT AAT CCA CAA ACA GGA CAA TCA ACA GGC CTC TTG GGC AAT CGT TGG TTC TAC TTG
   1 M   N   N   P   Q   T   G   Q   S   T   G   L   L   G   N   R   W   F   Y   L
  61 GTA TTA GCA GTT TTG CTG ATG TGT ATG ATC TCG GGT GTC CAA TAT TCC TGG ACA CTG TAC
  21 V   L   A   V   L   L   M   C   M   I   S   G   V   Q   Y   S   W   T   L   Y
 121 GCT AAC CCG GTT AAA GAC AAC CTT GGC GTT TCT TTG GCT GCG GTT CAG ACG GCT TTC ACA
  41 A   N   P   V   K   D   N   L   G   V   S   L   A   A   V   Q   T   A   F   T
 181 CTC TCT CAG GTC ATT CAA GCT GGT TCT CAG CCT GGT GGT GGT TAC TTC GTT GAT AAA TTC
  61 L   S   Q   V   I   Q   A   G   S   Q   P   G   G   G   Y   F   V   D   K   F
 241 GGT CCA AGA ATT CCA TTG ATG TTC GGT GGT GCG ATG GTT CTC GCT GGC TGG ACC TTC ATG
  81 G   P   R   I   P   L   M   F   G   G   A   M   V   L   A   G   W   T   F   M
 301 GGT ATG GTT GAC AGT GTT CCT GCT CTG TAT GCT CTT TAT ACT CTG GCC GGT GCA GGT GTT
 101 G   M   V   D   S   V   P   A   L   Y   A   L   Y   T   L   A   G   A   G   V
 361 GGT ATC GTT TAC GGT ATC GCG ATG AAC ACG GCT AAC AGA TGG TTC CCG GAC AAA CGC GGT
 121 G   I   V   Y   G   I   A   M   N   T   A   N   R   W   F   P   D   K   R   G
 421 CTG GCT TCC GGT TTC ACC GCT GCC GGT TAC GGT CTG GGT GTT CTG CCG TTC CTG CCA CTG
 141 L   A   S   G   F   T   A   A   G   Y   G   L   G   V   L   P   F   L   P   L
 481 ATC AGC TCC GTT CTG AAA GTT GAA GGT GTT GGC GCA GCA TTC ATG TAC ACC GGT TTG ATC
 161 I   S   S   V   L   K   V   E   G   V   G   A   A   F   M   Y   T   G   L   I
 541 ATG GGT ATC CTG ATT ATC CTG ATC GCT TTC GTT ATC CGT TTC CCT GGC CAG CAA GGC GCC
 181 M   G   I   L   I   I   L   I   A   F   V   I   R   F   P   G   Q   Q   G   A
 601 AAA AAA CAA ATC GTT GTT ACC GAC AAG GAT TTC AAT TCT GGC GAA ATG CTG AGA ACA CCA
 201 K   K   Q   I   V   V   T   D   K   D   F   N   S   G   E   M   L   R   T   P
 661 CAA TTC TGG GTT CTG TGG ACC GCA TTC TTT TCC GTT AAC TTT GGT GGT TTG CTG CTG GTT
 221 Q   F   W   V   L   W   T   A   F   F   S   V   N   F   G   G   L   L   L   V
 721 GCC AAC AGC GTC CCT TAC GGT CGC AGC CTC GGT CTT GCC GCA GGT GTG CTG ACG ATC GGT
 241 A   N   S   V   P   Y   G   R   S   L   G   L   A   A   G   V   L   T   I   G
 781 GTT TCG ATC CAG AAC CTG TTC AAT GGT GGT TGC CGT CCT TTC TGG GGT TTC GTT TCC GAT
 261 V   S   I   Q   N   L   F   N   G   G   C   R   P   F   W   G   F   V   S   D
 841 AAA ATC GGC CGT TAC AAA ACC ATG TCC GTC GTT TTC GGT ATC AAT GCT GTT GTT CTC GCA
 281 K   I   G   R   Y   K   T   M   S   V   V   F   G   I   N   A   V   V   L   A
 901 CTT TTC CCG ACG ATT GCT GCC TTG GGC GAT GTA GCC TTT ATC GCC ATG TTG GCA ATC GCA
 301 L   F   P   T   I   A   A   L   G   D   V   A   F   I   A   M   L   A   I   A
 961 TTC TTC ACA TGG GGT GGT AGC TAC GCT CTG TTC CCA TCG ACC AAC AGC GAT ATT TTC GGT
 321 F   F   T   W   G   G   S   Y   A   L   F   P   S   T   N   S   D   I   F   G
1021 ACG GCA TAC TCT GCC AGA AAC TAT GGT TTC TTC TGG GCT GCA AAA GCA ACT GCC TCG ATC
 341 T   A   Y   S   A   R   N   Y   G   F   F   W   A   A   K   A   T   A   S   I
1081 TTC GGT GGT GGT CTG GGT GCT GCA ATT GCA ACC AAC TTC GGA TGG AAT ACC GCT TTC CTG
 361 F   G   G   G   L   G   A   A   I   A   T   N   F   G   W   N   T   A   F   L
1141 ATT ACT GCG ATT ACT TCT TTC ATC GCA TTT GCT CTG GCT ACC TTC GTT ATT CCA AGA ATG
 381 I   T   A   I   T   S   F   I   A   F   A   L   A   T   F   V   I   P   R   M
1201 GGC CGT CCA GTC AAG AAA ATG GTC AAA TTG TCT CCA GAA GAA AAA GCT GTA CAT
 401 G   R   P   V   K   K   M   V   K   L   S   P   E   E   K   A   V   H
```

OXLT SEQUENCE AND ITS USE

CROSS REFERENCE PARAGRAPH

This application claims the benefit of U.S. Provisional Application No. 60/038,345, filed Feb. 27, 1997.

FEDERALLY SPONSORED RESEARCH OR DEVELOPMENT

This invention was made with Government support under grants from the National Science Foundation and the National Institutes of Health. The Government has certain rights to this invention.

FIELD OF THE INVENTION

The present invention relates to a novel gene which encodes the OxlT protein, its nucleotide sequence, its protein sequence and its use as an essential component in a three protein oxalate/formate exchange system.

BACKGROUND OF THE INVENTION

Urolithiasis, or urinary stone disease, is a common urinary tract problem afflicting more than 10% of the U.S. population. Urinary tract stones are most frequently (70%) composed of calcium oxalate alone or calcium oxalate mixed with calcium phosphate. Thus, the management of oxalate in individuals susceptible to urolithiasis is especially important (U.S. Pat. No. 5,286,495).

The majority of oxalate in plasma and urine is derived from the endogenous metabolism of ascorbic acid, glyoxylate, and to a lesser degree, tryptophan. In addition, between 10% and 20% of the urinary oxalate is absorbed from the diet, especially through ingestion of leafy vegetables such as spinach and rhubarb. Ingestion of ethylene glycol, diethylene glycol, xylitol, and excess ascorbic acid can lead to excess levels of oxalate following metabolic conversion. Use of methoxyflurane as an anaesthetic can also lead to oxalosis. Aspergillosis, which is an infection involving an oxalate-producing fungus, can lead to production and deposition of calcium oxalate (U.S. Pat. No. 5,286,495). It is believed that lowering the oxalate levels in the plasma, and subsequently the urine, would decrease the incidence of calcium oxalate stone formation.

Excess serum oxalic acid levels can also be related to genetic disorders. Primary hyperoxaluria is a general term for an inherited disorder which reveals itself in childhood and progresses to renal failure and frequently death in adolescence. It is characterized by high urinary excretion of oxalate and recurring calcium oxalate kidney stones. There are no satisfactory treatments for the two types of primary hyperoxaluria. Hemodialysis and renal transplantation have not been successful in halting the progress of this disease. A controlled diet is also an unsuccessful treatment for primary hyperoxaluria (U.S. Pat. No. 5,286,495).

Oxalate toxicity can also cause the poisoning of livestock, who may graze on oxalate-rich pastures containing plants which are high in oxalic acid such as *Halogeton glomeratus, Bassia hyssopifolia, Oxalis pescaprae,* and *Setaria sphacelata,* or grains infected with the oxalate-producing fungi *Aspergillus niger.* Chronic poisoning is often accompanied by appetite loss and renal impairment. Acute toxicity can lead to tetany, coma and death (Hodgkinson, A. [1977] *Oxalic acid in biology and medicine,* London: Academic Press, pp 220–222).

Three mechanisms for oxalate catabolism are known: oxidation, decarboxylation, and activation followed by decarboxylation (Hodgkinson, A. [1977], supra at 119–124). Oxalate oxidases are enzymes that are found in mosses, higher plants, and possibly fungi which catalyze the oxidation of oxalate to hydrogen peroxide plus carbon dioxide: $(COOH)_2 + O_2 \rightarrow 2CO_2 + H_2O_2$. Oxalate decarboxylases are enzymes which produce $CO_2$ and formate as products of oxalate degradation. An oxalate decarboxylase found in fungi catalyzes the decarboxylation of oxalic acid to yield stoichiometric quantities of formic acid and $CO_2$: $(COOH)_2 \rightarrow CO_2 + HCOOH$. Varieties of both aerobic and anaerobic bacteria can also degrade oxalic acid. An activation and decarboxylation mechanism is used for degradation of oxalate in *Pseudomonas oxalaticus* and other bacteria (U.S. Pat. No. 5,286,495).

*Oxalobacter fonnigenes* is a gram-negative anaerobe found in the soil and also in the mammalian intestine, where it plays a significant role in degradation of dietary oxalic acid. A critical limitation of anaerobic growth for this and other anaerobes is explained by the "uncoupling model". During fermentative growth, fermentation end products which include organic acids and alcohols build up in the cytoplasm leading to an acidification of the cytoplasm and a reduction in the internal pH to critical levels. The organic acids act as protonophores; a build up of which results in an inward flux of $H^+$. The rapid influx of $H^+$ counteracts the natural proton extrusion mechanisms needed to alkalinize the cytoplasm. The net result is a breakdown of the proton motive force essential to energy requiring membrane associated processes such as active transport of solutes and ions. Also associated with this phenomenon is a diminishing of intracellular ATP generation which has been observed to decrease growth yield. Kashket, E. R. (1987) *FEMS Microbiol. Rev.* 46:233–244. Large scale fermentation is frequently utilized by those in the biotechnical and pharmaceutical industries for product production. It would therefor be beneficial for industrial processes to have a system which is capable of ameliorating the energy deficit produced during fermentative growth and thereby increasing culture longevity and product yield.

Figure 1:
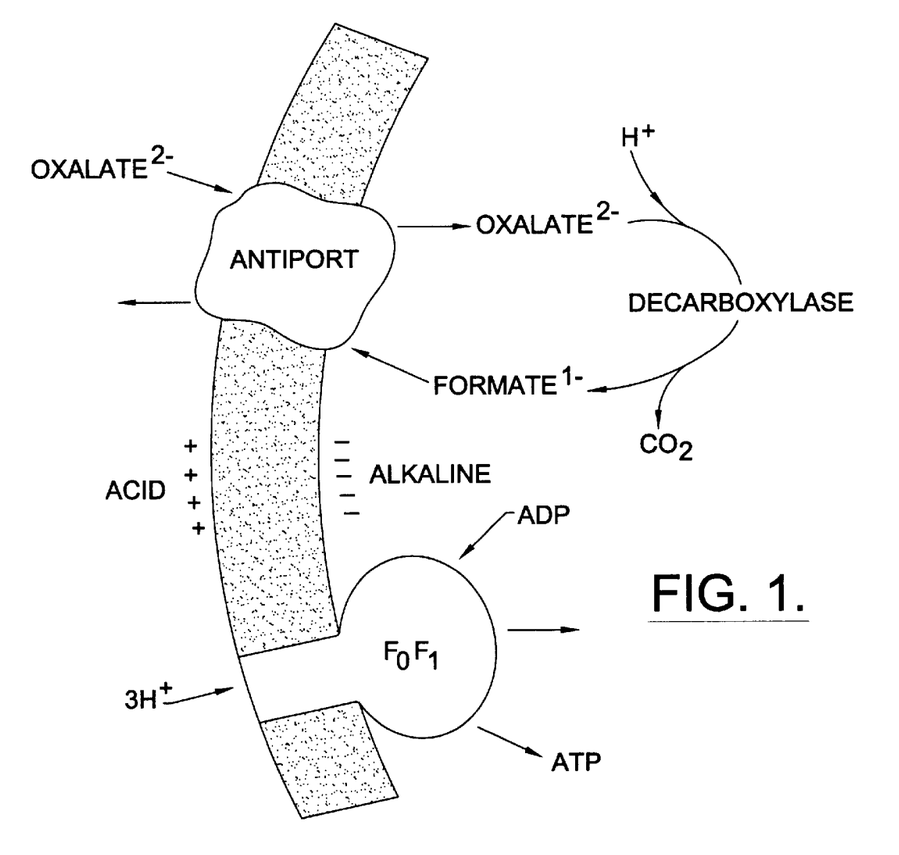
FIG. 1. A diagram illustrating the electrogenic $oxalate^{2-}$: $formate^{1-}$ exchange that forms the basis for sustaining a proton-motive force in *O. formigenes*. In this system, entry of the divalent oxalate is followed by its decarboxylation in a reaction that consumes $H^+$ to yield formate plus carbon dioxide. In turn, formate leaves by way of the exchange reaction. This general cycle (influx, decarboxylation, efflux) constitutes an $H^+$ pump with stoichiometry of $1H^+$/turnover, and given a stoichiometry of $3H^+$/ATP formation, oxalate decarboxylation could support ATP synthesis by $F_0F_1$ with a P:Ox ratio of 1:3.

*Oxalobacter formigenes* derives metabolic energy from the decarboxylation of oxalate during a "proton-motive metabolic cycle". See Anantharam et al. (1989) *J. Biol. Chem.* 264, 7244–7250 and Maloney, P. C. (1995) *Curr. Opin. Cell Biol.* 6:571–582. In this cycle, the entry of divalent oxalate is coupled to the exit of its decarboxylation product, monovalent formate, resulting in formation of a membrane potential that is internally negative. Because the intracellular oxalate decarboxylation consumes a cytosolic proton, the entry of negative charge is accompanied in a stoichiometric fashion by appearance of an internal hydroxyl anion. As a result, the combined activity of the vectorial antiport reaction and the scalar decarboxylation step comprises a thermodynamic proton pump. In this way, *O. formigenes* establishes the proton-motive force required for both the synthesis of ATP, by reversal of a DCCD (dicyclohexylcarbodiimide)-sensitive ATPase, and for the support of other membrane reactions requiring a proton-motive force (See FIG. 1).

Experiments based on the reconstitution of activity from crude detergent extracts suggest the oxalate/formate exchange reaction is mediated by a conventional membrane carrier. See Anantharam et al. (1989) *J. Biol. Chem.* 264:7244–7250. This reasoning is reinforced by the finding that oxalate transport is catalyzed by a single protein, OxlT, whose SDS-PAGE mobility (ca. 38 kDa) resembles that of other bacterial carrier protein. See Ruan et al. (1992) *J. Biol. Chem.* 267:10537–10543. For this reason, the present invention includes the cloning and sequencing of OxlT.

Although OxlT is the sole protein required for import of oxalate and export of formate, two other proteins are required for the decarboxylation of oxalate in *O. formigenes*: oxalyl-CoA decarboxylase (Lung et al. (1991) *Amer. J. Kidney Dis.* 17:381–385) and formyl-CoA transferase (Sidhu et al. (1997) *J. Bacteriol.* 179:3378–3381). The isolation of the three proteins will allow the reconstitution of the thermodynamic proton pump from *Oxalobacter formigenes*. By reconstituting expression of the genes encoding the three proteins in a fermentative bacterium, cell survival could be prolonged during production of a cell product by using oxalate as an additional energy source resulting in a intracellular increase in ATP production. In this manner the invention could be used in industrial fermentation processes to increase product yield by extending culture longevity which is adversely affected by low intracellular ATP levels or by low proton motive force values. It has been demonstrated that individuals with enteric hyperoxauria and recurrent calcium oxalate stone formation lack intestinal colonization by *Oxalobacter formigenes*. See Allison et al. (1986) *J. Nutr.* 116:455–460; Goldkin et al. (1985) *Am. J. Gastroenterol.* 80:860; and Kleinschmidt et al. (1993) *Urolithiasis* 2. Plenum Press, New York, N.Y. It can therefore be envisioned that the reconstituted pump may have medical and veterinary applications in the reduction of elevated serum oxalate levels associated with the formation of kidney stones and other medical disorders.

SUMMARY OF THE INVENTION

A DNA sequence encoding a transport protein responsible for the physical movement of oxylate and formate across the plasma membrane is provided. The protein, OxlT, can be isolated from the gram negative anaerobe, *Oxalobacter formigenes*. The protein is part of the three protein oxylate/formate antiport exchange system that allows for conversion of extracellular oxylate to formate+$CO_2$.

The OxlT coding sequence can be used to provide a metabolic energy system to the cell. The system comprises the OxlT transport protein in combination with oxalylCoA decarboxylase and formyl-CoA transferase. Expression cassettes can be designed to express all or part of the system in a target host. Such energy generating systems can be used in industrial settings that utilize fermentation. The energy generating systems of the invention extend culture longevity and increase product yield.

In another aspect of the invention, the OxlT coding sequence can be used in pharmaceutical compositions for manipulating serum oxalic acid levels in patients in need thereof. In this manner, liposomes comprising the energy generating system can be developed and administered to humans and other animals.

BRIEF DESCRIPTION OF THE DRAWINGS

FIG. 2. OxlT DNA and amino acid sequences. The DNA sequence (SEQ ID NO: 4) encoding OxlT is shown. The corresponding amino acid sequence (SEQ ID NOS: 4 and 5) is also given, with predicted transmembrance segments underlined.

FIGS. 3A and 3B. Hydropathy profile and topological model of OxlT. (3A) Proposed topological model of OxlT, derived from an analysis of hydropathy (3B) and from consideration of the distribution of charged residues. Negatively charged residues (D,E) are shown as gray squares, and except for K355, positively charged residues (R,K) are given as solid circles. Enlarged circles show the expected locations of C28, C271 and K355. (3B) Hydropathy profile of the OxlT amino acid sequence, performed according to Kyte & Doolittle using a window of 13 residues.

FIG. 4. OxlT expressed in *E. coli* catalyzes the electrogenic exchange of formate and oxalate. The detergent extracts of IPTG-induced and uninduced cells were used to prepare proteoliposomes loaded with potassium formate or NMG formate, as described below. To begin the transport reaction, proteoliposomes were diluted into NMG- or potassium-based assay media (as shown) containing 100 μM [$^{14}$C] oxalate, with 1 μM valinomycin or the equivalent amount of carrier ethanol. Samples were taken for filtration and washing at the indicated times. The presence of external potassium ($K_O$), internal potassium ($K_I$) or no potassium (no K) is indicated on the graph.

DETAILED DESCRIPTION OF THE INVENTION

The present invention relates to the isolation of a novel DNA sequence which encodes the protein responsible for the transport of extracellular oxalate into the cell and the extrusion of formate, a product of oxalate's catabolism from the cell. The DNA sequence of the invention was isolated from *Oxalobacter formigenes* and encodes the protein OxlT. Provided in the invention is OxlT's nucleotide sequence (SEQ ID NO: 4) as well as the amino acid sequence of the OxlT protein (SEQ ID NOS: 4 and 5).

The nucleotide sequence of the invention set forth in SEQ ID NO: 4 has applications in biotechnology as a means of improving culture longevity and product yield during industrial fermentation processes. The nucleotide sequence also has medical and veterinary applications which include methods of manipulating serum oxalate levels in humans and other animals.

Using the sequence information set forth in SEQ ID NOS: 4 and 5, other DNA sequences can be isolated based on sequence homology at either the amino acid or nucleotide sequence level. Any suitable molecular method can be used to identify and isolate such sequences including, but not limited to, PCR amplification, genome sequencing and DNA hybridization. In the same manner, synthetic nucleotide sequences can be designed based on the amino acid sequences of the invention. Methods to design and make such synthetic sequences are available in the art. See, for example, Perlak et al. (1991) *Proc. Natl. Acad. Sci. USA* 88:3324–3328; and Murray et al. (1989)) *Nucleic Acids Research* 17:477–498.

In a hybridization method, the hybridization probes may be genomic DNA fragments, cDNA fragments, RNA fragments, or other oligonucleotides, and may be labeled with a detectable group such as $^{32}$p, or any other detectable marker. Probes for hybridization can be made by labeling synthetic oligonucleotides based on the sequences of the invention. Degenerate primers designed on the basis of conserved amino acid sequences can additionally be used. Preparation of probes for hybridization is generally known in the art and is disclosed in Sambrook et al., *Molecular Cloning: A Laboratory Manual* (2d ed., 1989); and Ausebel et al. *Current Protocols in Molecular Biology*, John Wiley & Sons (1998), hereby incorporated by reference. The labeled probes can be used to screen cDNA or genomic libraries. Methods for construction of such cDNA and genomic libraries are generally known in the art and are disclosed in Sambrook et al., *Molecular Cloning: A Laboratory Manual* (2d.ed. 1989); and Ausebel et al. *Current Protocols in Molecular Biology*, John Wiley & Sons (1998).

In a PCR method, the DNA or amino acid sequence of the invention can be aligned with other known sequences of similar function and nucleotide primers can be designed based on any conserved short stretches of amino acid sequences or nucleotide sequences. Pairs of primers can be used in PCR reactions for amplification of DNA sequences from cDNA or genomic DNA. In addition, a single specific primer with a sequence corresponding to the nucleotide sequence disclosed herein can be paired with a primer having a sequence of the DNA vector in the cDNA or genomic libraries for PCR amplification of the sequences 5' or 3' to the nucleotide sequence disclosed herein. Methods for designing PCR primers and PCR cloning are generally known in the art and are disclosed in Sambrook et al., *Molecular Cloning: A Laboratory Manual* (2d ed., 1989); and Ausebel et al. *Current Protocols in Molecular Biology*, John Wiley & Sons (1998).

The sequences of the invention comprise transport proteins in other organisms that may be isolated according to well known techniques based on their sequence homology to the sequence set forth herein. In these techniques all or part of the known sequence is used as a probe which selectively hybridizes to other possible transport protein sequences present in a population of cloned genomic DNA fragments or cDNA fragments (i.e. genomic or cDNA libraries) from a chosen organism.

Additionally, antibodies can be prepared against substantially pure preparations of the protein of the invention. See, for example, Radka 35 U.S.C. et al. (1983) *J. Immunol.* 128:2804; and Radka et al. (1984) *Immunogenetics* 19:63. It is recognized that any combination of methods may be utilized to purify proteins and/or DNA sequences of the invention.

Conditions that will permit other DNA sequences to hybridize to the DNA sequences disclosed herein can be determined in accordance with techniques generally known in the art. For example, hybridization of such sequences may be carried out under conditions of reduced stringency, medium stringency, or high stringency (e.g., conditions represented by a wash stringency of 35–40% Formamide with 5× Denhardt's solution, 0.5% SDS, and 1 × SSPE at 37° C.; conditions represented by a wash stringency of 40–45% Formanide with 5× Denhardt's solution, 0.5% SDS, and 1 × SSPE at 42° C.; and conditions represented by a wash stringency of 50% Formainide with 5× Denhardt's solution, 0.5% SDS, and 1 × SSPE at 42° C., respectively. See Sambrook et al., *Molecular Cloning, A Laboratory Manual* (2d. ed., 1989); and Ausebel et al. *Current Protocols in Molecular Biology*, John Wiley & Sons (1998)). In general, sequences which promote membrane associated transport of oxalate and formate and hybridize to the DNA sequences disclosed herein will be at least 70–75% homologous, 80–85% homologous, and even 90–95% homologous or more.

The following terms are used to describe the sequence relationships between two or more nucleic acids or polynucleotides: (a) "reference sequence", (b) "comparison window", (c) "sequence identity", (d) "percentage of sequence identity", and (e) "substantial identity". (a)As used herein, "reference sequence" is a defined sequence used as a. basis for sequence comparison. A reference sequence may be a subset of or the entire specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237–244 (1988); Higgins and Sharp, *CABIOS* 5:151–153 (1989); Corpet, et al., *Nucleic Acids Research* 16:10881–90 (1988); Huang, et al., *Computer Applications in the Biosciences* 8:155–65 (1992), and Person, et al., *Methods of Molecular Biology* 24:307–331 (1994); preferred computer alignment methods also include the BLASTP, BLASTN, and BLASTX algorithms. Altschul, et al., *J. Mol. Biol.* 215:403–410 (1990). Alignment is also often performed by visual inspection and manual alignment.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not substantially change the functional properties of the molecule. When sequences differ in conservative substitutions, the present sequence identity may be adjusted upwards to correct for the conservative nature of the substitution. Sequences which differ by such conservative substitutions are said to have "sequence similarity " or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy. Amino acid sequences for these purposes normally means sequence identity of at least 60%, more preferably at least 70%, 80%, 90%, and most preferably at least 95%. Polypeptides which are "substantially similar" share sequences as noted above except that residue positions which are not identical may differ by conservative amino acid changes.

Another indication that nucleotide sequences are substantially identical is if two molecules hybridize to each other under stringent conditions. Generally, stringent temperature conditions are selected to be about 5° C. to about 20° C. lower than the melting point ($T_m$) for the specific sequence at a defined ionic strength and pH. The denaturation or melting of DNA occurs over a narrow temperature range and represents the disruption of the double helix into its complementary single strands. The process usually is characterized by the temperature of the midpoint of transition, $T_m$, which is sometimes described as the melting temperature. Formulas are available in the art for the determination of melting temperatures. Typically, stringent wash conditions are those in which the salt concentration is about 0.02 molar at pH 7 and the temperature is at 50, 55, or 60° C. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

The nucleotide and peptide sequences of the invention may be altered in various ways including amino acid substitutions, deletions, truncations, and insertions. Methods for such manipulations are generally known in the art. For example, amino acid sequence variants of the peptides and proteins can be prepared by mutations in the DNA. Methods for mutagenesis and nucleotide sequence alterations are well known in the art. See, for example, Kunkel, T. (1985) *Proc. Natl. Acad. Sci. USA* 82:488–492; Kunkel et al. (1987) *Methods in Enzymol.* 154:367–382; U.S. Pat. No. 4,873,192; Walker and Gaastra (eds.) *Techniques in Molecular Biology*, MacMillan Publishing Company, NY (1983) and the references cited therein. Thus, the nucleotide sequences of the invention include both the naturally occurring sequences as well as mutant forms. Likewise, the peptides and proteins of the invention encompass both naturally occurring and modified forms thereof. Such variants will continue to possess the desired activity. Obviously, the mutations that will be made in the DNA encoding the variant must not place the sequence out of reading frame and preferably will not create sequences deleterious to expression of the gene product. See, EP Patent Application Publication No. 75,444.

Thus proteins of the invention include the naturally occurring forms as well as variants thereof. These variants will be substantially homologous and functionally equivalent to the native protein. A variant of a native protein is "substantially homologous" to the native protein when at least about 80%, more preferably at least about 90%, and most preferably at least about 95% of its amino acid sequence is identical to the amino acid sequence of the native protein. A variant may differ by as few as 1, 2, 3, or 4 amino acids. By "functionally equivalent" is intended that the sequence of the variant defines a chain that produces a protein having substantially the same biological activity as the native protein of interest. Such functionally equivalent variants that comprise substantial sequence variations are also encompassed by the invention. Thus a functionally equivalent variant of the native protein will have a sufficient biological activity to be therapeutically useful. By "therapeutically useful" is intended effective in achieving a therapeutic goal, as for example, lowering internal oxalic acid levels in a patient in need thereof.

Methods are available in the art for determining functional equivalence. Biological activity can be measured using assays specifically designed for measuring activity of the native protein, including assays described in the present invention. Additionally, antibodies raised against the biologically active native protein can be tested for their ability to bind to the functionally equivalent variant, where effective binding is indicative of a protein having conformation similar to that of the native protein.

DNA sequences can also be synthesized chemically or modified by site-directed mutagenesis to reflect the codon preference of the host cell and increase the expression efficiency.

The proteins of the invention can be "engineered" in accordance with the present invention by chemical methods or molecular biology techniques. Molecular biology methods are most convenient since proteins can be engineered by manipulating the DNA sequences encoding them. Genomic DNA, cDNA, synthetic DNA, and any combination thereof may be used for this purpose. Genomic DNA sequences or cDNA sequences encoding proteins can be isolated based on the amino acid sequence of proteins or certain protein properties. Many methods of sequence isolation are known in the art of molecular biology. See particularly Sambrook et al. (1989) *Molecular Cloning: A Laboratory Manual* (Cold Spring Harbor Laboratory Press, Plainview, N.Y.), herein incorporated by reference.

In one embodiment the sequences of the invention may be used to construct an energy generating system which comprises the OxlT protein in combination with, oxalyl-CoA decarboxylase, and formyl-CoA transferase. These three components when together present within a host cell form the complete oxalate/formate exchange system. By "complete oxalate/formate exchange system" is intended that all necessary protein catalyzed activity and reactions are operable, contained within the system, and capable of promoting oxalate importation, oxalate decarboxylation and formate exportation. Oxalyl-CoA decarboxylase catalyzes the reaction that converts oxalate to formate and $CO_2$. Formyl-CoA transferase is responsible for the activation of oxalate through delivery of a residue of coenzyme A to the reaction and OxlT is the transport protein that promotes both the import of oxalate into the cell and the export of formate out of the cell. The presence within the cell of all three proteins and their respective catalytic activities produces an elevated membrane potential and/or pH gradient, or "proton motive force" required for ATP production and other membrane associated energy requiring events. Both genes for oxalyl-CoA decarboxylase and formyl-CoA transferase have been cloned and sequenced and are described in publications Sidhu et al. (1997) *J Bacteriol.* 179:3378–3381; and Lung et al. (1991) *Amer. J of Kidney Dis.* 17:381–385 which are herein incorporated by reference.

Likewise, other proteins with similar functions as oxalyl-CoA decarboxylase and formyl-CoA transferase, isolated in the above described manner, may be used in concert with the OxlT protein or proteins of similar function to form a complete transport system. By "complete transport system" is intended that all components necessary to carry out the importation decarboxylation and exportation processes are present and functional.

The sequences of the invention can be used to create recombinant DNA molecules which comprise the OxlT sequence alone or in combination with the gene encoding the oxalyl-CoA decarboxylase and/or the gene encoding the formyl-CoA transferase.

The sequences of the invention can be used to construct expression cassettes for expression in suitable hosts including both prokaryotes and eukaryotes. Examples of suitable host systems include but are not limited to *Clostridium Kluyveri, Lactobacillus delbruekii, Lactobacillus bulgaricus, Lactobacillus reuteri, Streptococcus salivarus, Streptococcus thermophilous, Bacillus subtilis, Streptomyces venezeulae, Aspergillus niger, Streptomyces erythaeus, Saccharomyces cerevisiae, Escherichia coli, Peniciillium notatum* and *Pseudomonas syringae*.

The expression cassettes containing the gene or genes of interest will comprise transcriptional initiation regions linked to the gene(s) of interest. Such an expression cassette is provided with a plurality of restriction sites for convenient insertion of the nucleotide sequences of the invention behind the regulatory control of a designated promoter. Promoters that may be selected to control the expression of the gene or genes of interest will depend upon the host organism. Promoters may be chosen based on their strength and/or inducibility and/or host specificity. Suitable promoters include but are not limited to the lambda $P_R$, lambda $P_L$, tyr (tRNA), rrD1, rrnX1, rrnDXE, rrE1, rrnA1, rrnA2, T7 promoters (A1, A2, A3), T5 promoters, the bla gene promoter, tp1, GAL1, and LACZ. Likewise the native promoter of the sequences of the invention may be used. The transcriptional initiation region and the promoter, may be native or analogous or foreign or heterologous to the host. Additionally, the promoter may be the natural sequence or alternatively a synthetic sequence. By foreign is intended that the transcriptional initiation region is not found in the native host system into which the transcriptional initiation region is introduced.

The expression cassettes may comprise a single coding sequence or multiple sequences linked to a suitable promoter. When multiple sequences make up a single expression cassette the sequences may be arranged in any order so long as they are in the correct orientation with respect to the promoter and the direction of transcription. Methods of producing multi-gene expression cassettes that are stably maintained and expressed in a prokaryotic and eukaryotic hosts are known. See Rees and Hay (1995) *J. Biochem.* 309:999–1007; Stamford et al. (1996) *J. Biochem.* 313:335–342; and Huder and Dimroth (1995) *J. Bacteriol.* 177:3623–3630. By "multi-gene" or "multi-sequence expression cassette" is intended as an expressing cassette comprising more than one gene or sequence operably linked to a functional promoter producing a single nucleic acid molecule that is capable of being expressed in a target host. The term "sequence" as used in the phrase "multiple sequence expression cassette" is intended as any nucleotide or peptide sequence which can carry out the reaction or reactions required to form a complete transport system. With multiple sequence expression cassettes each sequence in the cassette may be under the control of its own promoter or the entire multiple sequence construction may be controlled by a single promoter. Alternatively the sequences of the invention can be contained on separate expression cassettes, each expression cassette being used to express the gene(s) independently within the host system.

Where appropriate, the gene(s) may be optimized for increased expression in the transformed host. That is, the genes can be synthesized using host specific preferred codons for improved expression. For example if *E. coli* were the system, only codons found in highly expressed *E. coli* proteins would be used. Methods for the optimization of genes through the use of preferred codons in order to improve their expression in *E. coli* can be found in U.S. Pat. No. 4,897,471 herein incorporated by reference. Should a host other than *E. coli* be used, such as a yeast or another bacterial strain, care would be taken to use codons preferred by that organism.

A multiple sequence expression cassette under the control of one promoter will be transcribed as one mRNA transcript. In order to optimize translation efficiency it may be preferable to modify the sequence positioning such that each sequence is sufficiently removed from the others to promote proper ribosomal binding to the ribosomal binding sites (Shine-Delgarno sequences). Methods of producing multiple gene expression cassettes are known in the art and are described in Rees and Hay (1995) *J. Biochem.* 309:999–1007; Stamford et al. (1996) *J. Biochem.* 313:335–342; Huder and Dimroth (1995) *J. Bacteriol.* 177:3623–3630; and U.S. Pat. 5,375,543.

A preferred embodiment of the invention would comprise a multi-sequence expression cassette comprising the genes encoding the oxalyl-CoA decarboxylase, the formyl-CoA transferase and the oxalate/formate transport protein (OxlT) operably linked together and sufficiently spaced promoting efficient ribosomal binding and hence translation initiation to the MRNA transcript. The genes will be linked to a single functional promoter sufficiently strong so as to allow complete processing or "read through" by the hosts native RNA polymerase producing a single completely processed MRNA transcript. By "read though" is intended that the hosts RNA polymerase produces a single transcript which comprises the mRNA complement of each gene contained on the expression cassette.

The transcriptional cassette will include in the 5'3' direction of transcription, a transcriptional and translational initiation region, a DNA sequence(s) of interest, and a transcriptional and translational termination region functional in the selected host system. The termination region may be native with the transcriptional initiation region, may be native with the DNA sequence of interest, or may be derived from another source. Convenient termination regions include the Trp operon att region and the His operon att region from *E. coli*. See Lee et al. (1978) *J. Mol Biol.* 121:193–217; and Frunzio et al. (1981) *Proc. Natl. Acad Sci. USA*, 78:2767–2771.

In order to express an engineered expression cassette in a suitable host system, the DNA encoding the engineered protein preferably is incorporated into a vector to form a transformation construct. There are numerous vectors known in the art for expression in different systems. The vector used for this invention can be a plasmid vector or a viral vector. The vector used should at least comprise an origin of replication, a promoter, a transcription termination signal, a selection marker for plasmid propagation and maintenance, a selection marker for transformed cells, a ribosome binding site, and a translation termination signal such as poly(A). A polylinker having multiple restriction enzyme sites for convenient cloning of heterologous DNA sequences may also be included. In addition, particularly in the *E. coli* system, it may be preferred to include the region coding for the amino- or carboxy-terminal domain of another protein to act as a carrier, wherein the protein to be expressed will be in the form of a stable fusion protein.

Other techniques that are used to regulate transcription, increase translation efficiency, prevent mRNA or protein degradation, enhance protein secretion, and ensure posttranslational processing and modification can be found in Goeddel, ed. (1990) *Methods in Enzymology*, Vol. 185 (Academic Press Ltd., London), herein incorporated by reference. In preparing the transformation construct, the various DNA fragments may be arranged to place the DNA sequences in the proper orientation and reading frame. Toward this end, adapters or linkers may be employed to join the DNA fragments. Other methods also may be utilized to provide for convenient restriction sites, removal of superfluous DNA, removal of restriction sites, or the like. Such methods involve DNA insertions, deletions, or substitutions, e.g. transitions and transversions. For these purposes, in vitro mutagenesis, primer repair, restriction, annealing, resection, ligation, PCR, or the like may be employed.

If more than one plasmid or vector is necessary for the purposes of this invention and the host to be transformed is bacteria the plasmids used must be from different complementation groups in order to insure proper maintenance, segregation, and propagation.

It is further recognized that the components of the transformation construct may be modified to increase expression. For example, truncated sequences, nucleotide substitutions, or other modifications may be employed. See, for example, Perlak et al. (1991) *Proc. Natl. Acad. Sci. USA* 88:3324–3328; Murray et al. (1989) *Nucleic Acids Res.* 17:477–498; and WO 91/16432.

The transformation constructs of the present invention can be introduced into any suitable target host, both eukaryotic (yeast, etc.) and prokaryotic, particularly bacteria hosts. In this manner, genetically modified hosts can be obtained. Protocols used to introduce DNA into the recipient host may vary depending on the target organism. In a preferred embodiment a bacteria or yeast host is to be transformed. Suitable methods of introducing DNA into recipient bacteria are known to those of ordinary skill in the art and include conjugation, transformation, transduction and electroporation.

Where the target to be transformed is yeast, methods of introducing DNA into yeast hosts include but are not limited to transformation and electroporation. Protocols for these techniques are available in Sambrook et al. (1989) *Molecular Cloning: A Lab Manual*, $2^{nd}$ Ed. Cold Spring Harbor Laboratory, Cold Spring Harbor N.Y. and Ausubel et al. *Current Protocols in Molecular Biology*, J. Wiley and Sons which are herein incorporated by reference.

The energy generating system of the invention is useful for increasing culture longevity and end-product production in a fermentation process, comprising: (i) transfecting the fermentation host with an expression vector as described and (ii) conducting said fermentation process in the presence of oxalic acid such that the time of production is lengthened via the generation of ATP. Methods for using recombinant hosts in industrial fermentation processes are known in the art.

The compositions and methods of the invention also find use in manipulating serum oxalic acid levels in mammals in need thereof. Such methods comprise administering to a patient a pharmaceutical composition comprising the complete oxalate/formate exchange system described above. Generally, such pharmaceutical compositions include liposomes, proteoliposomes, recombinant vector systems and the like.

The science of forming proteoliposomes is now well developed. Liposomes are unilamellar or multilamellar vesicles, having a membrane portion formed of lipophilic material and an interior aqueous portion. Methods for synthesizing such liposomes are known and available to those of skill in the art, as described in, e.g., Szoka et al. (1980) *Ann. Rev. Biophys. Bioeng.* 9:467; U.S. Pat. Nos. 4,235,871; 4,501,728 and 4,837,028, all of which are herein incorporated by reference. Liposomes of the present invention typically contain a functional combination of the energy-generating complex cf proteins wherein OxlT is incorporated into the membrane of the liposome and the soluble oxalyl-CoA decarboxylase and formyl-CoA transferase proteins are entrapped inside such that the complex performs as a functional oxalate:formate antiport. Alternatively, the proteins may be constructed as fusion proteins to a membrane localizing domain. The utility of proteoliposomes for delivery of drugs and other physiologically active agents is known in the art. See U.S. Pat. No. 5,616,341; and U.S. Pat. No. 4,873,089.

Another method of administering the oxalate/formate exchange system to a patient (animal or human) is through the use of probiotics. The utility of "probiotic microorganisms" or microorganisms which offer physiological and/or immunological health benefits to humans and/or animals is also widely known. See U.S. Pat. Nos. 5,635,202; 5,604,127; and 5,478,557. In this manner it is foreseen that bacterial host cells expressing the oxalate/formate exchange system can be introduced into humans or animals for manipulating internal oxalic acid levels. In one embodiment, the bacterial host cells expressing the oxalate/formate exchange system may be bacteria normally associated with the intestinal microflora of humans or animals. In this capacity the bacteria expressing the system may be administered orally so that the bacteria can move naturally through the digestive tract and colonize the intestine. It is foreseen that bacteria which have successfully colonized the intestine and which are expressing the system described above will serve to lower internal oxalate levels through the process of oxalate uptake and subsequent conversion to formate and $CO_2$.

Since the three-component energy generating system has particular utility in the manipulation of excess serum oxalate levels which may lead to serious disorders in humans and animals, such as urolithiasis, and acute oxalic acid toxicity, the present invention also includes pharmaceutical compositions comprising the disclosed compounds. The compositions of the present invention can be formulated according to known methods to prepare pharmaceutically useful compositions, such as by admixture with a pharmaceutically acceptable carrier vehicle. Suitable vehicles and their formulation are described, for example, in Remington's Pharmaceutical Sciences (16th ed., Osol, A. (ed.), Mack, Easton Pa. (1980)). In order to form a pharmaceutically acceptable composition suitable for effective administration, such compositions will contain an effective amount of the composition with internal oxalic acid lowering ability, either alone, or with a suitable amount of carrier vehicle.

It is contemplated that the compositions of the present invention will be administered by an individual in therapeutically effective amounts. That is, in an amount sufficient to lower internal oxalic acid levels in a patient in need thereof, such as those afflicted with the diseases primary hyperoxaluria or urolithiasis caused by excess internal oxalic acid. The effective amount of the composition will vary according to the weight, sex, age, and medical history of the individual. Other factors which influence the effective amount may include, but are not limited to, the severity of the patient's condition, internal oxalic acid level, the stability of the composition, the kinetics of the compositions ability to sequester internal oxalic acid, previous exposure to the composition, kidney of other disease, etc.

Additional pharmaceutical methods may be employed to control the duration of action. Controlled release preparations may be achieved by the use of polymers to complex or absorb the compositions. The controlled delivery may be exercised by selecting appropriate macro molecules (for example, polyesters, polyamino acids, polyvinyl pyrrolidone, ethylene-vinylacetate, methylcellulose, carboxymethylcellulose, or protamine sulfate). The rate of drug release may also be controlled by altering the concentration of such macromolecules.

Another possible method for controlling the duration of action comprises incorporating the therapeutic agents into particles of a polymeric substance such as polyesters, polyamino acids, hydrogels, poly(lactic acid) or ethylene vinylacetate copolymers. Alternatively, it is possible to entrap the therapeutic agents in microcapsules prepared, for example, by coacervation techniques or by interfacial polymerization, for example, by the use of hydroxymethyl cellulose or gelatin-microcapsules or poly (methylmethacrylate) microcapsules, respectively, or in a colloid drug delivery system, for example, liposomes, albumin, microspheres, microemulsions, nanoparticles, nanocapsules, or in macroemulsions. Such teachings are disclosed in Remington's Pharmaceutical Sciences (1980).

The pharmaceutically prepared compositions of the invention may be provided to a patient by means well known in the art. Such means of introduction include oral means, intranasal means, subcutaneous means, intramuscular means, intravenous means, intraarterial means, or parenteral means.

The dosage of composition administered will vary depending upon pharmacodynamic characteristics of the compound, its mode and route of administration, the age, health, and weight of the recipient, the nature and extend of the oxalosis, and any concurrent treatments. Generally, the pharmaceutical composition will be administered to supply the protein at a concentration circulating in the blood generally in the range of about 50 µg or less, preferably about 100 µg or less, more preferably about 500 µg or less. Other issues pertaining to dosage and administration will be apparent to one skilled in the art in view of the present disclosure.

Having now generally described this invention, the same will be better understood by reference to certain specific examples which are included herein for purposes of illustration only, and are not intended to be limiting of the invention, unless specified.

EXPERIMENTAL

Genes encoding the oxalyl-CoA decarboxylase (Lung et al. (1991) Amer. J. Kidney Dis. 17:381–385) and formyl-CoA tiansferase (Sidhu et al. (1997) J. Bacteriol. 179:3378–3381) proteins from O. formigenes have been cloned.

E. coli strain KW251 (Promega) was used for the screening of an O. formigenes lambda phage library, and subcloning of positive restriction fragments was performed using pBluescript II KS– ($Amp^r$) carried in strain XL1 blue ($Tet^r$) (Stratagene). Strain XL1 blue harboring pMS421 ($spec^r$, $LacI^q$) was identified as strain XL3 and was used for expression of OxlT from pBKOxlTSK+, a pBluescript II SK+ derivative in which the gene encoding OxlT is placed under control of the lac promoter. Cells were grown aerobically at 37° C. in Luria Broth, with drugs as required (100 µg/ml carbenicillin, 12 µg/ml tetracycline, 50 µg/ml spectinomycin).

EXAMPLE 1. CLONING OF THE OxlT FULL LENGTH GENE.

O. formigenes Genomic DNA. Cells of O. formigenes, were the source of genomic DNA used in preliminary hybridization experiments. DNA was extracted using the East DNA extraction kit of Invitrogen.

OxlT was purified as described in Ruan et al. (1992) J. Biol. Chem. 267:10537–10543. After removing lipid from the peak activity fraction appearing on CM-Sepharose chromatography, 100 µg purified OxlT was subjected to SDS-PAGE and transferred at 4° C. to an Applied Biosystem ProBlott PVDF membrane at 100 V for 1 hr, using a transfer solution containing 25 mM Tris, 10 mM glycine and 0.5 mM dithiotreitol. The membrane with adsorbed OxlT was washed four times with distilled water and provided to the Harvard Microchemistry Facility (Cambridge, Mass.), which reported NNPQTGQSTGLLGNRWFYLV (single letter amino acid code) (SEQ ID NO: 1) as the probable N-terminal sequence; there was some indication of a ragged N-terminus.

Based on the N-terminal amino acid sequence noted above, two degenerate oligonucleotide probes were prepared. Oligo 1 had the nucleotide sequence, AAC/T-AAC/T-CCI-CAA/G-ACI-GGI-CA (I indicates inosine) (SEQ ID NO: 2), corresponding to residue nos. 1–7 of the N-terminal sequence; Oligo2, AAC/T-A/CGI-TGG-TTC/T-TAC/T-C/TT (SEQ ID NO: 3), corresponded to residue nos 14–19. In preliminary work, Southern hybridization at 42° C. with Oligo 2 gave a unique hybridization band using O. formigenes genomic DNA digested completely by EcoRI, HindIII, or PstI. Oligo1 showed this same pattern, but also hybridized to the λ-HindIII markers. Since the O. formigenes library was housed in lambda phage Oligo2 was used for our initial screens.

A library of O. formigenes genomic DNA had been constructed previously using the Promega lambda-GEM11 XhoI half-site arm vector. See Lung et al. (1991) Amer. J. Kidney Dis. 17:381–385. This library was screened with Oligo2 using the general procedures as described in Sambrook et al. (1989) Molecular Cloning: A Laboratory Manual, 2$^{nd}$ edition, Cold Spring Harbor Laboratory Press, Cold Spring Harbor, N.Y., observing a positive clone for every 3,000–5,000 plaques. After three rounds of plaque purification, insert fragments of 10–16 kb were identified by SacI digestion. SacI fragments were further digested with PstI and subcloned to eventually yield a 3.2 kb PstI-SacI fragment which showed hybridization to both Oligo1 and Oligo2. This positive fragment was placed in pBluescript II KS-, giving pBKOxlTKS-. A nested deletion series was prepared for sequencing. After identification of the gene encoding OxlT, the DNA sequence in this region was confirmed by second-strand sequencing using plasmids selected from this same deletion series. Site-directed mutagenesis was then used to introduce an XbaI site 23 bp upstream from the likely OxlT start codon, ATG (see FIG. 2 and SEQ ID NO: 4), producing pBKOxlT-Xb. pBKOxlT-Xb was subsequently digested with XbaI plus HindIII to give a 1.4 kb fragment containing the complete gene encoding OxlT. This 1.4 kb fragment was ligated into the Xba-HindIII site of pBluescript II SK+ to generate pBKOxlTSK+, in which expression of OxlT was regulated by the lac promoter. As a final step, the E. coli strain XL3 was transformed with pBKOxlTSK+ for functional tests. The oxlT sequence has been deposited in GenBank (Accession No. U40075).

Double-stranded DNA was sequenced using the dideoxy chain-termination procedure as described in Sanger et al. (1977) Proc. Natl. Acad. Sci. USA 74:5463–5467. The nested deletion series was sequenced using universal primers for pBluescript II KS-; as primers for sequencing the opposite strand, appropriate complementary synthetic oligonucleotides were designed.

EXAMPLE 2. EXPRESSION OF OxlT IN E. coli AND WESTERN BLOTS CONFIRMING THE PRESENCE OF OxlTp A synthetic peptide of the N-terrninal portion of the peptide described above was synthesized. After conjugation of the peptide to bovine serum albumim, rabbit polyclonal antibody was raised against the material by Hazelton Research Products, Denver, Pa.

An overnight preculture of E. coli XL3, which carried pBKOxlTSK+ and pMS421, was diluted 100-fold in fresh media, and 1 mM IPTG was added 1 hr later. pMS421 is a middle-copy compatible plasmid encoding the gene LacI$^q$. This plasmid gave strong repression of OxlT expression in the absence of IPTG and allowed propagation of pBKOxlTSK+ without selective pressures accompanying unregulated protein expression. IPTG induced cells and uninduced control cells were harvested after an additional 4 hr growth.

SDS-PAGE with 12% acrylamide was performed as outlined by Laemmli, U. I. (1970) Nature 227:680–685. For routine imrnunoblots, protein was transferred to nitrocellulose using standard techniques, and after exposure to immune serum diluted 1/2500, binding of the primary antibody was detected in a chemiluminescence protocol (Amersham). See Crawford et al. (1991) Proc. Natl. Acad. Sci. USA 88:9262–9266. Antibody directed against the OxlT N-terminus reported expression of OxlT in IPTG-induced cells carrying pBKOxlTSK+, but not in uninduced cells or in cells carrying the parent pBluescript II SK+ (± IPTG) (results not shown). It was also evident that the SDS-PAGE profile of OxlT expressed in E. coli resembled that of authentic OxlT, including the presence of both monomeric (ca. 38 kDa) and dimeric (ca. 75 kDa) forms of the protein.

Equally important, OxlT immunoreactivity coincided with acquisition by induced cells of a capacity to catalyze both the oxalate self-exchange reaction and the electrogenic exchange of oxalate and formate.

EXAMPLE 3. SOLUBILIZATION AND RECONSTITUTION OF OxlT AND ASSAYS OF TRANSPORT ACTIVITY (TWO METHODS).

IPTG-induced cells and uninduced control cells (each 5 mg protein) were harvested by centrifugation, resuspended in 5 ml of lysozyme (300 μg/ml) and DNase (40 μg/ml) and incubated at 37° C. for 10 min. Cells were repelleted and then resuspended in 5 ml of water. The resulting "ghosts" were spun down and resuspended in 0.5 ml ice-cold solubilization solution (25 mM MOPS/K, 20% [v/v] glycerol, 0.4% acetone/ether purified E. coli phospholipid, 1 mM DTT, 1.25% octyl-β-D-glucoside, 0.75 mM phenylmethylsulfonyl fluoride, 10 mM oxalate). After incubation at 4° C. for 20 min, the suspension was clarified by centrifugation at 4° C. in an Eppendorf refrigerated microfuge (15,000g×15 min) to give a crude detergent extract which was stored at −80° C. until use.

Figure 4:
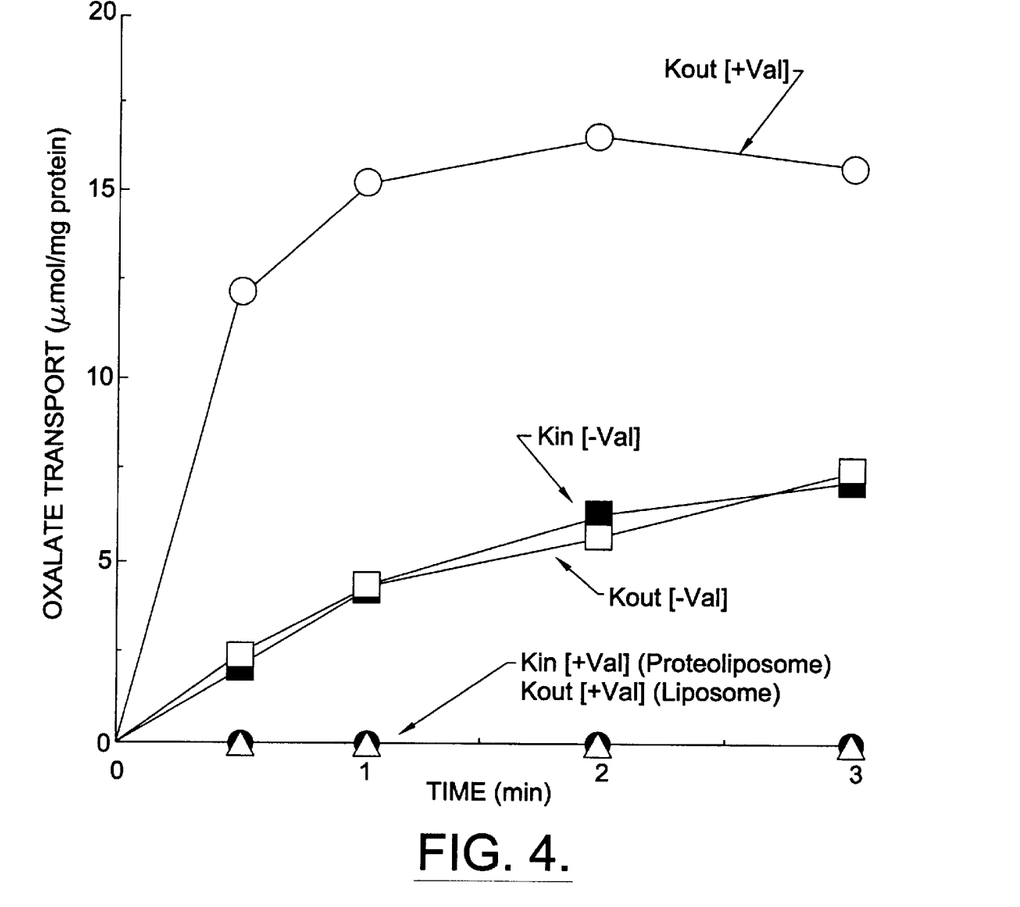

OxlT transport activity was monitored by reconstitution of protein into proteoliposomes. In a final volume of 250 μl, 50–100 μl of a detergent extract was mixed with 1.36 mg bath-sonicated liposomes, additional detergent (to 1.25%), and either 50 mM MOPS/K or 50 mM MOPS/NMG (pH7). After incubation at 4° C. for 20 min, proteoliposomes were formed at 23° C. by addition of 5 ml of a dilution and loading buffer (pH 7). Two methods were used to monitor OxlT transport activity, oxalate self exchange and oxalate/formate dual exchange. For estimates of oxalate self-exchange (Table 1), the loading buffer contained 100 mM potassium oxalate, 50 mM MOPS/K and 1 mM DTT. To assess oxalate/formate exchange (FIG. 4), the loading buffer was either 100 mM potassium formate or 100 mM NMG formate, along with 50 mM MOPS/K or 50 mM MOPS/NMG and 1 mM DTT. Formation of proteoliposomes was complete within 20 min.

In a rapid filtration assay to monitor oxalate self-exchange (Table 1), 0.2 ml of the proteoliposomal suspension was applied directly, under vacuum, to the center of a 0.22μ GSTF Millipore filter. The rapid filtration assay was done according to the methods described in Ambudkar et al. (1990) J. Biol. Chem. 265:12287–12292. The external medium was removed by two 5 ml rinses with assay buffer (100 mM $K_2SO_4$, 50 mM MOPS/K, pH7), and on release of the vacuum the assay began as proteoliposomes were covered with 0.25 ml of assay buffer containing 100 μM [$^{14}$C] oxalate. The reaction was termninated 3 min. later by filtration and three quick rinses with assay buffer. To examine oxalate self-exchange, oxalate-loaded proteoliposomes were washed free of external substrate by filtration on Millipore filters (0.22 μm pore size), and then, while still affixed to the filters, they were covered for 3 min with an assay medium containing 100 μM [$^{14}$C] oxalate before a final filtration and wash. This test (Table 1) gave no indication of oxalate transport by cells bearing pBluescriptII SK+ (±IPTG) (0.02 μmol/mg protein). By contrast, uninduced cells with pBKOxlTSK+ displayed a low but significantly positive signal (0. 14 μmol/mg protein), while IPTG induction led to markedly increased accumulation of label (2.3 μmol/mg protein) (Table 1).

Alternatively (FIG. 4), formate-loaded proteoliposomes were isolated by centrifugation (16) and resuspended in a small volume of the K- or NMG-based loading buffers. Subsequently, they were diluted 120-fold into either NMG or K-based assay buffers, as above, containing 100 μM [$^{14}$C] oxalate, with or without 1 μM valinomycin. In this way, it was possible to generate a membrane potential whose polarity was either interior positive (potassium outside, NMG inside) or interior negative (NMG outside, potassium inside). As the basis for comparison, proteoliposomes were either loaded with NMG-formate and tested in NMG-based assay buffer or proteoliposomes loaded with K-formate were assayed in a K-based assay buffer; the two sets of controls gave the same results. Results demonstrated that an imposition of an internally positive electrical potential strongly stimulated the oxalate transport observed in untreated controls, while imposition of an internally negative potential completely inhibited the reaction. Since the pKa's for oxalate are 1.23 and 3.83, the simplest model is that the OxlT transporter, whether expressed in *O. formigenes* or *E. coli*, mediates exchange of divalent oxalate and monovalent formate.

TABLE 1

Expression of oxalate self-exchange in *E. coli*

| Plasmid | Condition | Oxalate Transport (μmol/mg/protein/3 min) |
|---|---|---|
| pBluescript II SK+ | −IPTG | 0.02 |
| pBKOx1TSK+ | −IPTG | 0.14 |
| pBluescript II SK+ | +IPTG | 0.02 |
| pBKOx1TSK+ | +IPTG | 2.30 |

EXAMPLE 4. CHARACTERISTICS OF THE CLONED PROTEIN

Analysis of the deduced amino acid sequence of OxlT reveals a novel hydrophobic protein of 418 amino acid residues having a predicted mass of 44,128 daltons. No proteins with significant homology to OxlT were found in a BLITZ search of the Swiss Protein Database; similarly, no proteins were found related to the hypothetical hydrophilic protein specified by the OxlT non-coding strand.

Figure 3A:
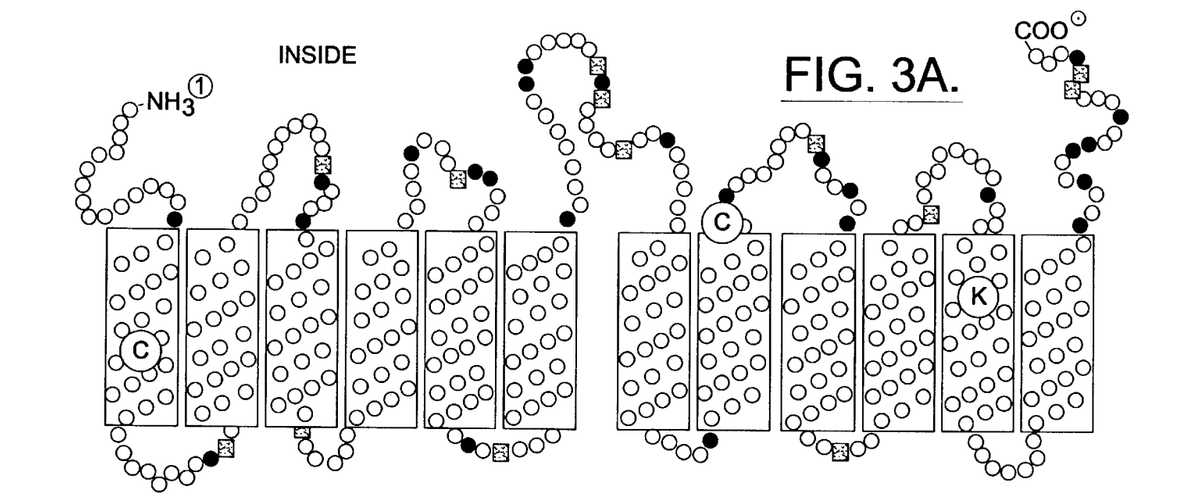
Figure 3B:
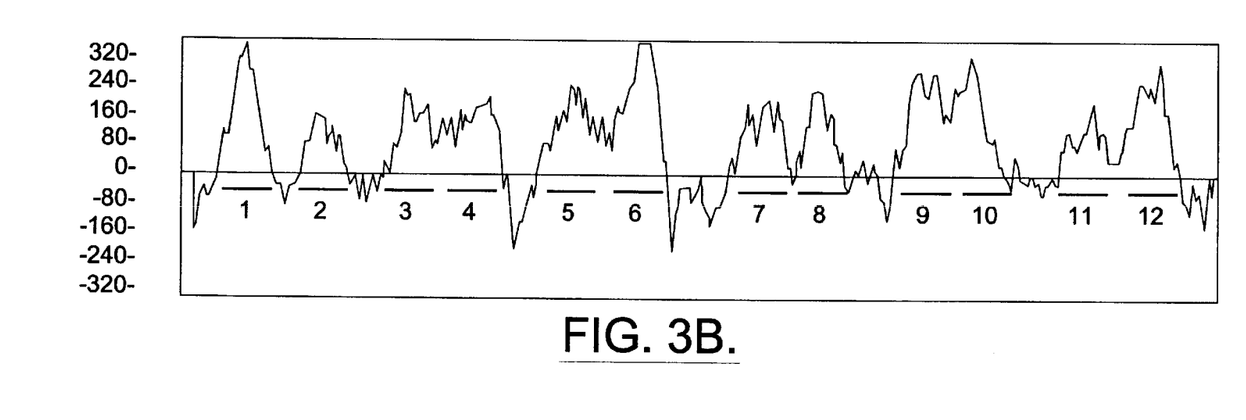

Analysis of OxlT hydropathy according to the method of Kyte and Doolittle (1982) *J. Mol. Biol.* 157:105–132; (FIG. 3) suggests the presence of 12 hydrophobic segments of sufficient length to constitute a transmembrane a-helix (TM1–12). A similar analysis according to Rost et al. (1995) *Protein Science* 4:521–533 predicts 11 transmembrane a-helices, including TM1 and TM3–12 (FIG. 3), but excluding TM2, whose hydropathy meets but does not exceed the cutoff value established by Kyte & Doolittle. Although membrane carriers with 11 transmembrane segments have been described in bacteria it is more typical to find examples with 10 or 12 transmembrane regions. For this reason, the initial model of OxlT topology (FIG. 3) assumes the 12 transmembrane segments identified by analysis of hydropathy. This initial model also conforms to the common finding of a central cytoplasmic loop that separates the regions containing TM1–6 and TM7–12.

The proposed OxlT structure was oriented with respect to cytoplasmic and extracellular phases, utilizing the observation of von Heijne, G. (1992) *J. Molec. Biol.* 225:487–494 that transmembrane segments often have an excess of positively charged residues at their cytoplasmic ends, especially in bacterial systems. It is evident that in the proposed structure (FIG. 3), charged residues are assigned to either the extracellular (net charge of 0) or cytoplasmic (net charge of +11) surfaces, with the exception of the single lysine residue (K355) that appears within TM11 (FIG. 3).

One main goal of the present invention was the cloning and sequencing of OxlT, the oxalate/formate antiport protein of *O. formigenes*. In particular, the cloned gene specifies the N-terminal sequence found in authentic OxlT (FIG. 2), and expression of this gene confers upon *E. coli* the capacity to mediate both the homologous self-exchange of oxalate and the heterologous, electrogenic exchange of oxalate with formate (Table 1, FIG. 4). Accordingly, it was concluded that this antiport protein retains its most important functional properties when expressed in *E. coli*. It is likely the main physical characteristics of OxlT are also preserved in *E. coli*, since the OxlT SDS-PAGE profiles in *E. coli* and *O. formigenes* are equivalent (data not shown), and since the positive response to an N-terminal peptide-directed antibody suggests OxlT retains its natural N-terminus.

Analysis of the OxlT amino acid sequence reveals a polytopic hydrophobic protein (FIG. 3) whose general structure resembles that of known membrane carriers in the several respects Maloney, P. C. (1995) *Curr. Opin. Cell Biology* (1994) 6:571–582.22; Maloney, P. C., and Wilson, T. H. (1996) in *Escherichia coli and Salmonella typhimurium. Cellular and Molecualr Biology*, 2$^{nd}$ edition (Neidhardt, F. et al., eds) Chapter 74, American Society for Microbiology, Washington, D.C. (in press); and Henderson, P. J. F. (1993) *Curr. Opin. Cell Biol.* 5:708–721: (I) the presence of 12 (or 11) presumed transmembrane segments; (ii) N- and C-terminal regions facing the cytoplasm (presuming an even number of transmembrane segments); (iii) the finding of a cytoplasmic loop midway along the sequence (r. 190–219), separating the region containing TM1–6 from that containing TM7–12; (iv) an excess of positively charged residues at the presumed cytoplasmic surface.

The OxlT predicted structure has two additional features deserving of specific comment. First, the presence of a single charged residue (K355) within TM11 should be noted (FIG. 3). Because OxlT substrates are anionic (oxalate$^{2-}$, formate$^{1-}$), the presence of this apparently uncompensated positive charge in the hydrophobic sector prompts the hypothesis that K355 forms part of an anionic binding center within the substrate translocation pathway. Preliminary tests are compatible with this idea, since several uncharged substitutions at position 355 give variants that fail to transport, while the K355R derivative retains activity. A second finding of interest is that OxlT has only two cysteine residues (C28, C271). Because neither of these cysteines is required for function, OxlT presents an attractive target for cysteine scanning mutagenesis, an approach that has proven valuable to the study of several membrane transport systems. See Akabas et al. (1992) *Science* 258:307–310; Jung et al. (1994) *Biochemistry* 33:3980–3985; Yan, R. T., and Maloney, P. C. (1995) *Proc. Natl. Acad. Sci. USA* 92:5973–5976.

Evaluation of oxalate transport (Table 1, FIG. 4) supports the idea that the main features of OxlT selectivity are retained in *E. coli*. Moreover, calculations using these data suggest the unusually high velocity of OxlT is also found in this expression system. OxlT appears present at somewhat higher levels in *E. coli* than in *O. formigenes,* since immunoblots gave slightly more staining for nearly equivalent amounts of membrane protein. Crude detergent extracts from induced *E. coli* yielded a stimulated oxalate/formate antiport rate of at least 24 μmol/min per mg of protein (FIG. 4), while in a comparable study using *O. formigenes,* an exchange rate of 16 μmol/min per mg protein was found. Such high velocity is unusual, even for a purified membrane carrier, but was anticipated for OxlT, which has the highest maximal velocity among known carriers of organic substrates.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated nucleic acid fragment encoding a polypeptide comprising the amino acid sequence set forth in SEQ ID NO:5.

2. An isolated nucleic acid fragment comprising the sequence set forth in SEQ ID No:4.

3. An isolated nucleic acid fragment comprising a nucleic acid sequence having 90% identity to the sequence set forth in SEQ ID NO:4 and encoding a polypeptide having oxalate/formate exchange activity.

4. An isolated nucleic acid fragment comprising a nucleic acid sequence encoding an amino acid sequence having 90% identity to the amino acid sequence set forth in SEQ ID NO:5 and oxalate/formate exchange activity.

5. An expression cassette comprising a promoter capable of expression in a target host operably linked to the nucleotide sequence set forth in SEQ ID NO:4.

6. The expression cassette of claim 5, wherein said cassette further comprises at least one additional coding sequence selected from the sequences encoding formyl-CoA transferase and oxalyl-CoA decarboxylase, said additional sequence operably linked to a functional promoter.

7. A vector comprising the expression cassette of claim 5.

8. A vector comprising the expression cassette of claim 6.

9. An expression cassette comprising a promoter capable of expression in a target host operably linked to a nucleotide sequence comprising a sequence having 90% identity to the sequence set forth in SEQ ID NO:4 and encoding a polypeptide having oxalated/formate exchange activity.

10. A vector comprising the expression cassette of claim 9.

11. The expression cassette of claim 9, wherein said cassette further comprises at least one additional coding sequence selected from the sequences encoding formyl-CoA transferase and oxalyl-CoA decarboxylase, said additional sequence operably linked to a functional promoter.

12. A vector comprising the expression cassette of claim 11.

* * * * *

UNITED STATES PATENT AND TRADEMARK OFFICE
CERTIFICATE OF CORRECTION

PATENT NO. : 6,162,632
DATED : December 19, 2000
INVENTOR(S) : Maloney et al.

It is certified that error appears in the above-identified patent and that said Letters Patent is hereby corrected as shown below:

ON THE TITLE PAGE
Item [54]
In the title "OXLT" should read --OxIT--.

Signed and Sealed this

Eighth Day of May, 2001

Attest:

NICHOLAS P. GODICI

Attesting Officer     Acting Director of the United States Patent and Trademark Office

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 20 amino acids
        (B) TYPE: amino acid
        (C) STRANDEDNESS: single
        (D) TOPOLOGY: linear     (ii) MOLECULE TYPE: peptide     (v) FRAGMENT TYPE: N-terminal     (vi) ORIGINAL SOURCE:
        (A) ORGANISM: Oxalobacter formigenes     (xi) SEQUENCE DESCRIPTION: SEQ ID NO:1:

```
Asn Asn Pro Gln Thr Gly Gln Ser Thr Gly Leu Leu Gly Asn Arg Trp
1               5                   10                  15

Phe Tyr Leu Val
            20
```

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Degenerate oligonucleotide
            probe"

(vi) ORIGINAL SOURCE:
        (A) ORGANISM: Oxalobacter formigenes     (xi) SEQUENCE DESCRIPTION: SEQ ID NO:2:

AAYAAYCCNC ARACNGGNCA                                          20

(2) INFORMATION FOR SEQ ID NO:3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Degenerate oligonucleotide
            probe"

(vi) ORIGINAL SOURCE:
        (A) ORGANISM: Oxalobacter formigenes     (xi) SEQUENCE DESCRIPTION: SEQ ID NO:3:

AAYMGNTGGT TYTAYYT                                                17

(2) INFORMATION FOR SEQ ID NO:4:

(i) SEQUENCE CHARACTERISTICS:
        (A) LENGTH: 1254 base pairs
        (B) TYPE: nucleic acid
        (C) STRANDEDNESS: single
        (D) TOPOLOGY: linear     (ii) MOLECULE TYPE: DNA (genomic)

(vi) ORIGINAL SOURCE:
        (A) ORGANISM: Oxalobacter formigenes     (ix) FEATURE:
        (A) NAME/KEY: CDS
        (B) LOCATION: 1..1254

(xi) SEQUENCE DESCRIPTION: SEQ ID NO:4:

```
ATG AAT AAT CCA CAA ACA GGA CAA TCA ACA GGC CTC TTG GGC AAT CGT        48
Met Asn Asn Pro Gln Thr Gly Gln Ser Thr Gly Leu Leu Gly Asn Arg
 1               5                  10                  15

TGG TTC TAC TTG GTA TTA GCA GTT TTG CTG ATG TGT ATG ATC TCG GGT        96
Trp Phe Tyr Leu Val Leu Ala Val Leu Leu Met Cys Met Ile Ser Gly
            20                  25                  30

GTC CAA TAT TCC TGG ACA CTG TAC GCT AAC CCG GTT AAA GAC AAC CTT       144
Val Gln Tyr Ser Trp Thr Leu Tyr Ala Asn Pro Val Lys Asp Asn Leu
        35                  40                  45

GGC GTT TCT TTG GCT GCG GTT CAG ACG GCT TTC ACA CTC TCT CAG GTC       192
Gly Val Ser Leu Ala Ala Val Gln Thr Ala Phe Thr Leu Ser Gln Val
 50                  55                  60

ATT CAA GCT GGT TCT CAG CCT GGT GGT GGT TAC TTC GTT GAT AAA TTC       240
Ile Gln Ala Gly Ser Gln Pro Gly Gly Gly Tyr Phe Val Asp Lys Phe
 65                  70                  75                  80

GGT CCA AGA ATT CCA TTG ATG TTC GGT GGT GCG ATG GTT CTC GCT GGC       288
Gly Pro Arg Ile Pro Leu Met Phe Gly Gly Ala Met Val Leu Ala Gly
                 85                  90                  95

TGG ACC TTC ATG GGT ATG GTT GAC AGT GTT CCT GCT CTG TAT GCT CTT       336
Trp Thr Phe Met Gly Met Val Asp Ser Val Pro Ala Leu Tyr Ala Leu
            100                 105                 110

TAT ACT CTG GCC GGT GCA GGT GTT GGT ATC GTT TAC GGT ATC GCG ATG       384
Tyr Thr Leu Ala Gly Ala Gly Val Gly Ile Val Tyr Gly Ile Ala Met
        115                 120                 125

AAC ACG GCT AAC AGA TGG TTC CCG GAC AAA CGC GGT CTG GCT TCC GGT       432
Asn Thr Ala Asn Arg Trp Phe Pro Asp Lys Arg Gly Leu Ala Ser Gly
130                 135                 140

TTC ACC GCT GCC GGT TAC GGT CTG GGT GTT CTG CCG TTC CTG CCA CTG       480
Phe Thr Ala Ala Gly Tyr Gly Leu Gly Val Leu Pro Phe Leu Pro Leu
145                 150                 155                 160
```

```
ATC AGC TCC GTT CTG AAA GTT GAA GGT GTT GGC GCA GCA TTC ATG TAC      528
Ile Ser Ser Val Leu Lys Val Glu Gly Val Gly Ala Ala Phe Met Tyr
            165                 170                 175

ACC GGT TTG ATC ATG GGT ATC CTG ATT ATC CTG ATC GCT TTC GTT ATC      576
Thr Gly Leu Ile Met Gly Ile Leu Ile Ile Leu Ile Ala Phe Val Ile
        180                 185                 190

CGT TTC CCT GGC CAG CAA GGC GCC AAA AAA CAA ATC GTT GTT ACC GAC      624
Arg Phe Pro Gly Gln Gln Gly Ala Lys Lys Gln Ile Val Val Thr Asp
            195                 200                 205

AAG GAT TTC AAT TCT GGC GAA ATG CTG AGA ACA CCA CAA TTC TGG GTT      672
Lys Asp Phe Asn Ser Gly Glu Met Leu Arg Thr Pro Gln Phe Trp Val
        210                 215                 220

CTG TGG ACC GCA TTC TTT TCC GTT AAC TTT GGT GGT TTG CTG CTG GTT      720
Leu Trp Thr Ala Phe Phe Ser Val Asn Phe Gly Gly Leu Leu Leu Val
225                 230                 235                 240

GCC AAC AGC GTC CCT TAC GGT CGC AGC CTC GGT CTT GCC GCA GGT GTG      768
Ala Asn Ser Val Pro Tyr Gly Arg Ser Leu Gly Leu Ala Ala Gly Val
        245                 250                 255

CTG ACG ATC GGT GTT TCG ATC CAG AAC CTG TTC AAT GGT GGT TGC CGT      816
Leu Thr Ile Gly Val Ser Ile Gln Asn Leu Phe Asn Gly Gly Cys Arg
            260                 265                 270

CCT TTC TGG GGT TTC GTT TCC GAT AAA ATC GGC CGT TAC AAA ACC ATG      864
Pro Phe Trp Gly Phe Val Ser Asp Lys Ile Gly Arg Tyr Lys Thr Met
        275                 280                 285

TCC GTC GTT TTC GGT ATC AAT GCT GTT GTT CTC GCA CTT TTC CCG ACG      912
Ser Val Val Phe Gly Ile Asn Ala Val Val Leu Ala Leu Phe Pro Thr
        290                 295                 300

ATT GCT GCC TTG GGC GAT GTA GCC TTT ATC GCC ATG TTG GCA ATC GCA      960
Ile Ala Ala Leu Gly Asp Val Ala Phe Ile Ala Met Leu Ala Ile Ala
305                 310                 315                 320

TTC TTC ACA TGG GGT GGT AGC TAC GCT CTG TTC CCA TCG ACC AAC AGC     1008
Phe Phe Thr Trp Gly Gly Ser Tyr Ala Leu Phe Pro Ser Thr Asn Ser
            325                 330                 335

GAT ATT TTC GGT ACG GCA TAC TCT GCC AGA AAC TAT GGT TTC TTC TGG     1056
Asp Ile Phe Gly Thr Ala Tyr Ser Ala Arg Asn Tyr Gly Phe Phe Trp
        340                 345                 350

GCT GCA AAA GCA ACT GCC TCG ATC TTC GGT GGT GGT CTG GGT GCT GCA     1104
Ala Ala Lys Ala Thr Ala Ser Ile Phe Gly Gly Gly Leu Gly Ala Ala
            355                 360                 365

ATT GCA ACC AAC TTC GGA TGG AAT ACC GCT TTC CTG ATT ACT GCG ATT     1152
Ile Ala Thr Asn Phe Gly Trp Asn Thr Ala Phe Leu Ile Thr Ala Ile
370                 375                 380

ACT TCT TTC ATC GCA TTT GCT CTG GCT ACC TTC GTT ATT CCA AGA ATG     1200
Thr Ser Phe Ile Ala Phe Ala Leu Ala Thr Phe Val Ile Pro Arg Met
385                 390                 395                 400

GGC CGT CCA GTC AAG AAA ATG GTC AAA TTG TCT CCA GAA GAA AAA GCT     1248
Gly Arg Pro Val Lys Lys Met Val Lys Leu Ser Pro Glu Glu Lys Ala
            405                 410                 415

GTA CAT                                                              1254
Val His (2) INFORMATION FOR SEQ ID NO:5:

(i) SEQUENCE CHARACTERISTICS:
        (A) LENGTH: 418 amino acids
        (B) TYPE: amino acid
        (D) TOPOLOGY: linear (ii) MOLECULE TYPE: protein (xi) SEQUENCE DESCRIPTION: SEQ ID NO:5:
```

-continued

```
Met Asn Pro Gln Thr Gly Gln Ser Thr Gly Leu Leu Gly Asn Arg
 1               5                  10                  15

Trp Phe Tyr Leu Val Leu Ala Val Leu Leu Met Cys Met Ile Ser Gly
            20                  25                  30

Val Gln Tyr Ser Trp Thr Leu Tyr Ala Asn Pro Val Lys Asp Asn Leu
        35                  40                  45

Gly Val Ser Leu Ala Ala Val Gln Thr Ala Phe Thr Leu Ser Gln Val
    50                  55                  60

Ile Gln Ala Gly Ser Gln Pro Gly Gly Tyr Phe Val Asp Lys Phe
65                  70                  75                  80

Gly Pro Arg Ile Pro Leu Met Phe Gly Ala Met Val Leu Ala Gly
                85                  90                  95

Trp Thr Phe Met Gly Met Val Asp Ser Val Pro Ala Leu Tyr Ala Leu
                100                 105                 110

Tyr Thr Leu Ala Gly Ala Gly Val Gly Ile Val Tyr Gly Ile Ala Met
            115                 120                 125

Asn Thr Ala Asn Arg Trp Phe Pro Asp Lys Arg Gly Leu Ala Ser Gly
130                 135                 140

Phe Thr Ala Ala Gly Tyr Gly Leu Gly Val Leu Pro Phe Leu Pro Leu
145                 150                 155                 160

Ile Ser Ser Val Leu Lys Val Glu Gly Val Gly Ala Ala Phe Met Tyr
                165                 170                 175

Thr Gly Leu Ile Met Gly Ile Leu Ile Ile Leu Ile Ala Phe Val Ile
                180                 185                 190

Arg Phe Pro Gly Gln Gln Gly Ala Lys Lys Gln Ile Val Val Thr Asp
            195                 200                 205

Lys Asp Phe Asn Ser Gly Glu Met Leu Arg Thr Pro Gln Phe Trp Val
            210                 215                 220

Leu Trp Thr Ala Phe Phe Ser Val Asn Phe Gly Gly Leu Leu Leu Val
225                 230                 235                 240

Ala Asn Ser Val Pro Tyr Gly Arg Ser Leu Gly Leu Ala Ala Gly Val
                245                 250                 255

Leu Thr Ile Gly Val Ser Ile Gln Asn Leu Phe Asn Gly Gly Cys Arg
                260                 265                 270

Pro Phe Trp Gly Phe Val Ser Asp Lys Ile Gly Arg Tyr Lys Thr Met
            275                 280                 285

Ser Val Val Phe Gly Ile Asn Ala Val Leu Ala Leu Phe Pro Thr
            290                 295                 300

Ile Ala Ala Leu Gly Asp Val Ala Phe Ile Ala Met Leu Ala Ile Ala
305                 310                 315                 320

Phe Phe Thr Trp Gly Gly Ser Tyr Ala Leu Phe Pro Ser Thr Asn Ser
            325                 330                 335

Asp Ile Phe Gly Thr Ala Tyr Ser Ala Arg Asn Tyr Gly Phe Phe Trp
            340                 345                 350

Ala Ala Lys Ala Thr Ala Ser Ile Phe Gly Gly Leu Gly Ala Ala
            355                 360                 365

Ile Ala Thr Asn Phe Gly Trp Asn Thr Ala Phe Leu Ile Thr Ala Ile
            370                 375                 380

Thr Ser Phe Ile Ala Phe Ala Leu Ala Thr Phe Val Ile Pro Arg Met
385                 390                 395                 400
```

-continued

```
Gly Arg Pro Val Lys Lys Met Val Lys Leu Ser Pro Glu Glu Lys Ala
                405                 410                 415
Val His
```